United States Patent [19]

Henkel et al.

[11] Patent Number: 4,698,300

[45] Date of Patent: Oct. 6, 1987

[54] PROCESS AND REAGENT FOR THE DETERMINATION OF α-AMYLASE

[75] Inventors: Eberhard Henkel, Hanover; Barkew Dolabdjian, Gross-Gerau; Roland Helger; Rainer Klink, both of Darmstadt; Uwe Würzburg, Dieburg, all of Fed. Rep. of Germany

[73] Assignee: Merck Patent Gesellschaft mit beschränkter Haftung, Darmstadt, Fed. Rep. of Germany

[21] Appl. No.: 625,482

[22] Filed: Jun. 28, 1984

[30] Foreign Application Priority Data

Jun. 28, 1983 [DE] Fed. Rep. of Germany ....... 3323245

[51] Int. Cl.[4] .......................... C12Q 1/34; C12Q 1/40
[52] U.S. Cl. ...................... 435/18; 435/22; 435/810
[58] Field of Search ............. 435/18, 22, 810

[56] References Cited

U.S. PATENT DOCUMENTS

| | | | |
|---|---|---|---|
| 4,102,747 | 7/1978 | Driscoll et al. | 435/22 |
| 4,145,527 | 3/1979 | Burns et al. | 536/120 X |
| 4,225,672 | 9/1980 | Hall | 435/74 |
| 4,233,403 | 11/1980 | Menson et al. | 435/22 |

FOREIGN PATENT DOCUMENTS

| | | |
|---|---|---|
| 1120836 | 3/1982 | Canada . |
| 2755803 | 6/1979 | Fed. Rep. of Germany . |
| 2004646 | 4/1979 | United Kingdom . |
| 2058780 | 4/1981 | United Kingdom . |

OTHER PUBLICATIONS

Wallenfels et al, Fresenius Z. Anal. Chem., 301, 169 (1980).

*Primary Examiner*—Esther M. Kepplinger
*Attorney, Agent, or Firm*—Millen & White

[57] ABSTRACT

A process and reagent are described for the determination of α-amylase by enzymatic splitting of an α-amylase substrate in the presence of α-glucosidase and β-glucosidase and measurement of a fission product. The substrate utilized is a 4-nitrophenyl-β,D-maltoheptaoside substituted in the phenyl ring by an electron withdrawing group, preferably a 2-chloro group.

7 Claims, 2 Drawing Figures

PROCESS AND REAGENT FOR THE DETERMINATION OF α-AMYLASE

BACKGROUND OF THE INVENTION

The present invention concerns a process and a reagent for the determination of α-amylase by enzymatic splitting of a substituted nitrophenylated maltoheptaoside, in which the aglycone is β-glycosidically bound, in the presence of α-glucosidase and β-glucosidase and measurement of the liberated aglycone.

The determination of the α-amylase activity in body fluids, e.g. serum, plasma, urine, duodenal juice, saliva, has a great importance in the clinical-chemical diagnosis for the recognition of pancreatic diseases.

The previously known methods for the determination of α-amylase depend upon the fact that starch is broken down by α-amylase and the fragments formed are determined spectrophotometrically. The important disadvantage of these methods is that starch, as the macromolecule, is difficult to characterize and to standardize.

Therefore, more recent methods use defined oligosaccharides as substrates. These are broken down in the presence of α-glucosidase as far as glucose, which is determined in per se known manner. (See, e.g. U.S. Pat. No. 4,000,042 and U.S. Pat. No. 3,879,263.) However, these reactions are very complex and are disturbed by endogenic glucose. A considerable simplification was achieved by the use of 4-nitrophenylated oligosaccharides with a chain length of 3 to 12 glucose units (G3–G12) as substrate for the α-amylase. By means of a subsequent α-glucosidase reaction, the liberated p-nitrophenol is measured (published Federal Republic of Germany Patent Application No. 27 31 421 and U.S. Pat. No. 4,233,403). In U.S. Pat. No. 4,145,527, there are described substrates for α-amylase with up to 6 glucose units, in the case of the production of which a mixture of the α- and β-isomers is always obtained, which is used together with α- and β-glucosidases. However, from Fresenius Z. Anal. Chem., 301, 169 (1980) it is known that with the β-isomers, in contradistinction to the α-isomers, substantially smaller activities are always measured. In addition, U.S. Pat. No. 4,102,747 discloses the determination of α-amylase using a mixture of α- and β-p-nitrophenyl isomers of G4–G10 oligosaccharides in combination with both α- and β-glucosidases. Similarly, DOS No. 2755803 discloses the use of G7 oligosaccharides having β-aglycones, including nitro- and dinitrophenyl, in combination with α- and β-glucosidases.

If, in the prior art, the p-nitrophenol is preferably used as the measured variable, then additional disadvantages arise: the pKa value of p-nitrophenol lies at 7.09; this means that, under optimum pH conditions for the course of the α-amylase determination (6.8–7.1), only about 50% of the liberated p-nitrophenol is present as colored phenolate anion and the resulting measurement signal is correspondingly low. Furthermore, changes in the hydrogen ion concentration of the test system, perhaps due to the use of acidic or alkaline samples, such as urine or duodenal juice, can change the degree of dissociation of the liberated p-nitrophenol and thus the apparent molar extinction coefficients.

SUMMARY OF THE INVENTION

Accordingly, it is an object of this invention to make available a process and a reagent for the determination of α-amylase with which the mentioned disadvantages can be avoided, and which enable a considerable increase in the detection sensitivity of the α-amylase.

Upon further study of the specification and appended claims, further objects and advantages of this invention will become apparent to those skilled in the art.

Surprisingly, it has been found that this problem can be solved by the use of a substituted 4-nitrophenyl-β, D-maltoheptaoside as substrate. Also surprising was the fact that the β-maltoheptaoside derivative is a better substrate for the α-amylase than the corresponding α-isomer since the opposite was known from the literature.

Thus, a subject of this invention is a process for the determination of α-amylase by enzymatic splitting of an α-amylase substrate in the presence of α-glucosidase and β-glucosidase and measurement of a fission product, wherein as substrate, there is used a 4-nitrophenyl-β, D-maltoheptaoside electronegatively substituted in the phenyl nucleus.

Furthermore, the invention concerns a reagent for the determination of α-amylase, containing essentially a 4-nitrophenyl-β,D-maltoheptaoside electronegatively substituted in the phenyl nucleus, an α-glucosidase and a β-glucosidase.

BRIEF DESCRIPTION OF THE DRAWINGS

Various other objects, features and attendant advantages of the present invention will be more fully appreciated as the same becomes better understood when considered in conjunction with the accompanying drawings, wherein.

DETAILED DISCUSSION

By introduction of electronegative substituents, i.e., electron withdrawing substituents, i.e. of substituents with —I— effect, such as e.g. nitro groups, cyanide groups, halogens, ester groups (e.g., COOR wherein R is $C_{1-6}$-alkyl), preferably halogens, such as chlorine, bromine, fluorine, especially chlorine, into the 4-nitrophenyl nucleus, the pKa value is displaced into the acidic region. The preferred substitution position is the 2-position in the nitrophenol. There is thereby achieved the additional advantage that the substituted 4-nitrophenol liberated by the reaction with glucosidase effects, under otherwise the same conditions, an increase in the sensitivity of the indicator reaction.

The substrate preferred according to the invention is 2-chloro-4-nitrophenyl-β,D-maltoheptaoside. For the splitting off of the β-positioned aglycone in the case of the α-amylase determination, it is necessary that, besides the α-glucosidase, β-gluucosidase must additionally also be used.

Typically, the phenyl ring attached to the maltoheptaoside is monosubstituted; however, it is also possible for additional substituents to be present, e.g., up to 4 substituents in total on the phenyl ring, preferably in the 2- and 3-positions.

Figure 1:
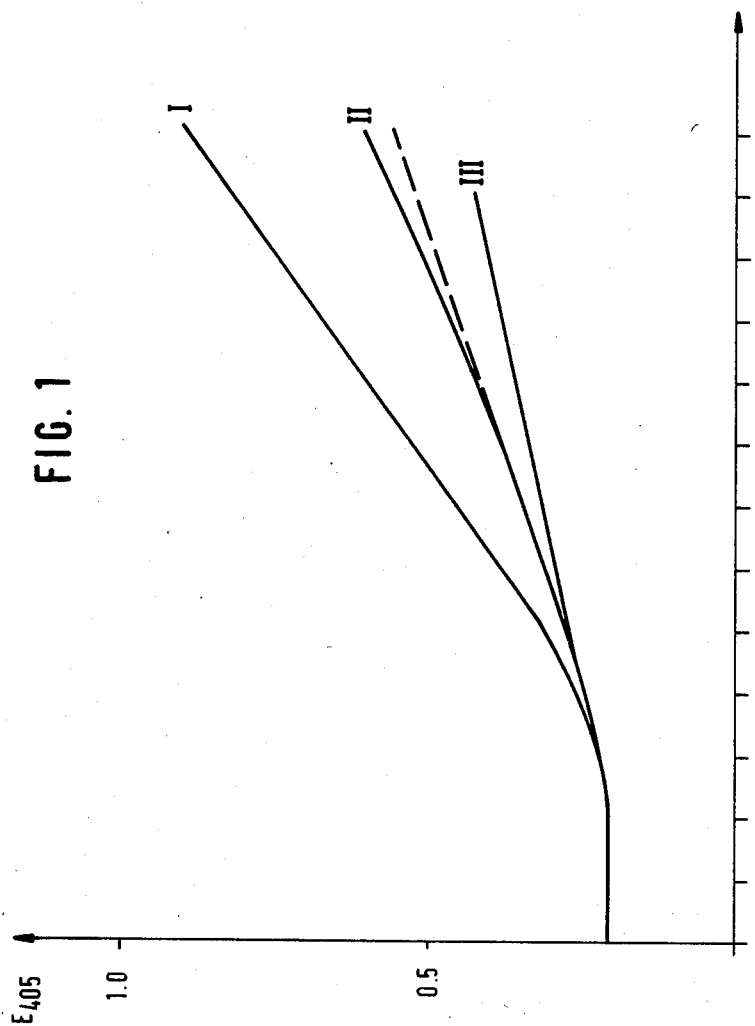
FIG. 1 shows the extinction coefficients observed in α-amylase determinations carried out using various substrates; I (this invention), II (prior art) and III (prior art)

Under the test conditions, with the substrates according to the invention, a measurement signal was to have been expected which is greater by a certain factor corresponding to the ratio of the extinction coefficients of e.g., halonitrophenol and 4-nitrophenol at 405 nm. Surprisingly, however, the measurement signal is substantially more strongly increases, which additionally considerably increases the sensitivity of the α-amylase determination according to the invention. FIG. 1 shows a comparison of the time-reaction curves in the case of the α-amylase determination between 2-chloro-4-nitrophenyl-β,D-maltoheptaoside (I) and the corresponding α-form (II), as well as with 4-nitrophenyl-α,D-maltoheptaoside (III). It thereby becomes clear that e.g. with 4-nitrophenyl-α,D-maltoheptaoside, there is achieved an extinction change per minute of 0.024; by chlorine substitution in the phenyl nucleus, this value is increased to 0.036; by transfer to the β-form, the extinction change per minute can be increased to above 0.075, i.e. by the factor 3. Besides the distinct absorption increase with the substrate according to the invention, in the case of 2-chloro-4-nitrophenyl-α,D-maltoheptaoside, a nonlinear course is to be seen in the curve.

The two isoenzymes pancrease α-amylase and saliva α-amylase display differing activities towards macromolecular substrates. Surprisingly, with the substrates according to the invention, these isoenzymes give the same activities.

In the case of the α-amylase determination, the substrates are split up by the α-amylase into smaller units (G3, G4) which, in turn, are broken down by the α-glucosidase as far as β-glucoside. The action of the β-glucosidase finally leads to the splitting off of the nitrophenol group, which serves as the measured variable.

The concentration of the substrate according to the invention in the test should amount to 0.1 to 300 mmol/l., preferably about 2 to 10 mmol/l. The concentration of the α-glucosidase usually lies in a range of $10^2$ to $2.5 \times 10^6$ U/l., preferably at about $8 \times 10^4$ U/l., that of the β-glucosidase in a range of $10^2$ to $10^5$ U/l., preferably at about $2.5 \times 10^3$ U/l.

For the carrying out of the process, buffer substances are necessary which can maintain as far as possible optimum pH conditions for the course of the α-amylase reaction, i.e. pH values of 5 to 9, preferably about 6.5 to 7.1. Suitable buffers include e.g. phosphate buffers, N-(2-hydroxyethyl)-piperazine-N-2-ethane-sulphonic acid (HEPES buffer), imidazole, triethanolamine, glycerol phosphate, preferably phosphate buffer. The concentration of the buffer should lie in the range of 10 to 200 mmol/l., preferably at about 50 mmol/l.

Apart from the mentioned components, the reagent according to the invention contains conventional amounts of a conventional activation agent, such as sodium or potassium chloride.

For the determination of α-amylase, the reagent solution of substrate, α-glucosidase, β-glucosidase, buffer and activation agent is mixed with the sample solution and the extinction recorded at 405 nm e.g. at 30° C. Typically, 0.2–3.0 ml of reagent is mixed with 1.0–50 μl of sample for ordinary α-amylase concentrations.

The reagent according to the invention is also suitable, in the form of absorbent materials impregnated therewith or incorporated into foils, as an indicator for the determination of α-amylase.

Unless indicated otherwise herein, the details of the reagent of this invention and of conducting the assay of this invention are essentially conventionally determinable in view of the state of the art, e.g., as described in U.S. Pat. Nos. 4,233,403, 4,145,527 and 4,102,747 and DOS No. 2,755,803 whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Determination of α-amylase

A reagent composition is prepared which, per ml. of test volume, contains the following components:

| reagent | concentration in the test |
| --- | --- |
| 2-chloro-4-nitrophenyl-β,D-maltoheptaoside | 5 mMol/l. |
| α-glucosidase | 80 U/ml. |
| β-glucosidase | 10 U/ml. |
| phosphate buffer (pH 6.8) | 0.05 Mol/l. |
| sodium chloride | 0.05 Mol/l. |
| Measurement conditions: | |
| temperature: 30° C. | |
| wavelength: 405 nm | |
| carrying out of the test: 1 ml. reagent + 10 μl. sample | |

A time-reaction curve with this reagent, in comparison with that of a version without substitution with halogen in the phenyl nucleus, is illustrated in FIG. 1.

In comparison with the line III (substrate: 4-nitrophenyl-α,D-maltoheptaoside), the line I shows (substrate: 2-chloro-4-nitrophenyl-β,D-maltoheptaoside) a distinct increase of the change of absorption ($\Delta$ E/min. ~0.05).

EXAMPLE 2

Determination of α-amylase, pH dependency of the absorption

Figure 2:
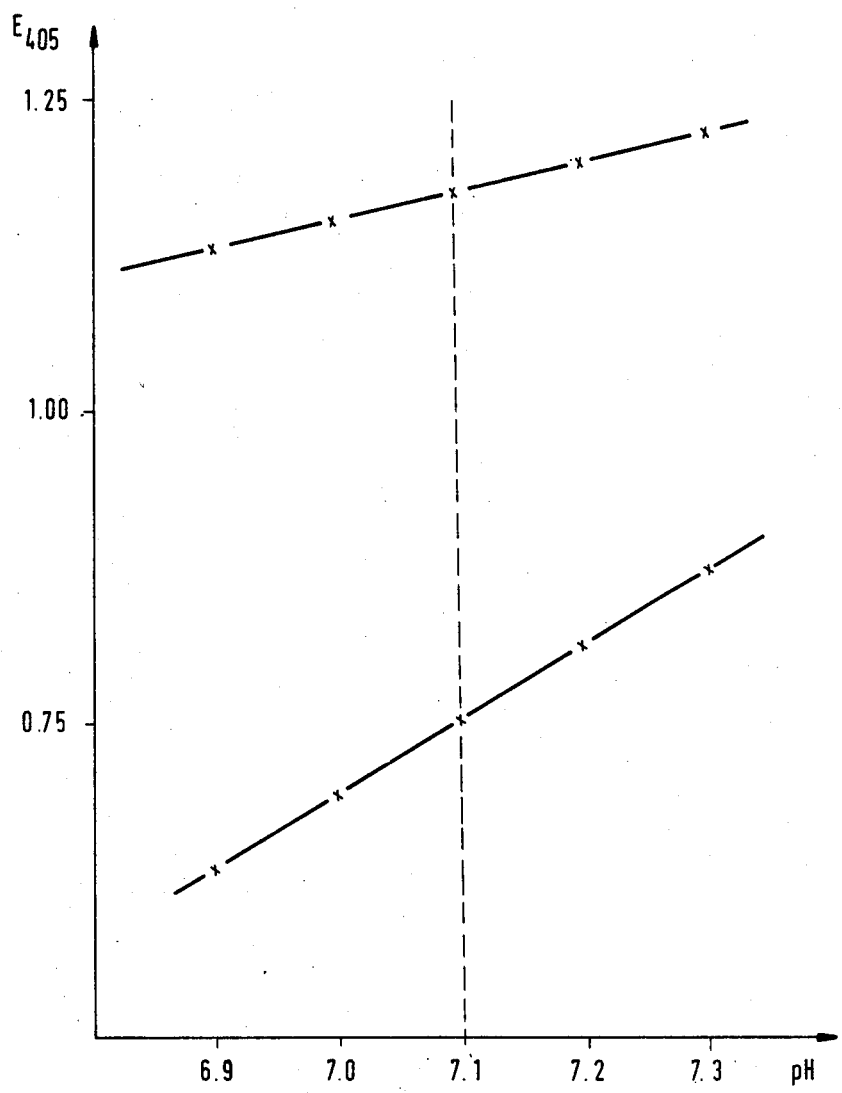
FIG. 2 shows the pH dependency of the absorption of the substrate of this invention (upper) and that of the prior art (lower).

Under the same conditions as in Example 1, there are measured the extinctions of two reagent solutions adjusted to a pH value of 7.1, one of which contains 2-chloro-4-nitrophenol, the other 4-nitrophenol. Subsequently, the pH values are slightly increased and decreased stepwise and the extinction deviations determined. FIG. 2 shows the result.

The smaller gradient of the upper line (reagent solution with 2-chloro-4-nitrophenol) shows that the extinction is less strongly influenced by change of the pH value than in the version with 4-nitrophenol (lower line).

EXAMPLE 3

Determination of α-amylase, comparison of the pure substrate (2-chloro-4-nitrophenyl-β,D-maltoheptaoside) with a mixture of α- and β-forms.

There is prepared the same reagent composition as in Example 1, with the difference that the substrate consists of equal parts of the α- and β-form. The amount of the extinction change lies, in the case of the use of this mixture, exactly between the values for the pure isomers.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the determination of $\alpha$-amylase in a sample comprising contacting the sample with $\alpha$-glucosidase, $\beta$-glucosidase, and a substrate for $\alpha$-amylase, wherein the substrate consists essentially of 2-chloro-4-nitrophenyl-$\beta$,D-maltoheptaoside, under conditions whereby said $\alpha$-amylase, $\alpha$-glucosidase and $\beta$-glucosidase will cleave the substituted 4-nitrophenyl group from the substrate, and measuring resultant cleaved substituted 4-nitrophenyl group to determine the amount of $\alpha$-amylase present in the sample.

2. A method of claim 1, wherein the concentrations during the determination are 0.1 to 300 mmole/l of substrate, $10^2$ to $2.5 \times 10^6$ U/l of $\alpha$-glucosidase and $10^2$ to $10^5$ U/l of $\beta$-glucosidase.

3. A method of claim 1, wherein the determination is conducted at a pH of 5 to 9 by addition to the sample of an effective amount of a buffer which achieves a pH of 5 to 9.

4. A method of claim 1, wherein the measurement is carried out spectrophotometrically.

5. A reagent kit for the determination of $\alpha$-amylase, consisting essentially of an $\alpha$-glucosidase, a $\beta$-glucosidase, and a 2-chloro-4-nitrophenyl-$\beta$,D-maltoheptaoside substrate, in amounts sufficient to quantitatively determine $\alpha$-amylase.

6. A reagent kit of claim 5, wherein the component concentrations are 0.1 to 300 mmole/l of substrate, $10^2$ to $2.5 \times 10^6$ U/l of $\alpha$-glucosidase and $10^2$ to $10^5$ U/l of $\beta$-glucosidase.

7. A reagent kit of claim 5, further comprising a buffer for the pH range of 5 to 9.

* * * * *